US007414128B2

(12) United States Patent
Ebdrup et al.

(10) Patent No.: US 7,414,128 B2
(45) Date of Patent: Aug. 19, 2008

(54) CRYSTALLINE R-GUANIDINES, ARGININE OR (L)-ARGININE (2S)-2-ETHOXY-3-{4-[2-(10H-PHENOXAZIN-10-YL) ETHOXY]PHENYL}PROPANOATE

(75) Inventors: Søren Ebdrup, København Ø (DK); Petra Christine Lugstein, Vienna (AT)

(73) Assignees: Dr. Reddy's Laboratories, Limited, Hyderabad (IN); Dr. Reddy's Laboratories, Inc., Bridgewater, NJ (US)

(*) Notice: Subject to any disclaimer, the term of this patent is extended or adjusted under 35 U.S.C. 154(b) by 0 days.

(21) Appl. No.: 11/079,161

(22) Filed: Mar. 14, 2005

(65) Prior Publication Data

US 2005/0159600 A1    Jul. 21, 2005

Related U.S. Application Data

(63) Continuation of application No. 10/209,567, filed on Jul. 30, 2002, now abandoned.

(51) Int. Cl.
| | |
|---|---|
| *C07D 265/38* | (2006.01) |
| *C07D 279/22* | (2006.01) |
| *A61K 31/54* | (2006.01) |
| *A61K 31/535* | (2006.01) |

(52) U.S. Cl. .............. 544/38; 544/42; 544/43; 544/102; 514/225.2; 514/225.8; 514/226.2

(58) Field of Classification Search ........... 544/102; 514/229.8
See application file for complete search history.

(56) References Cited

U.S. PATENT DOCUMENTS

| 6,054,453 A * | 4/2000 | Lohray et al. ............ 514/226.2 |
| 6,440,961 B1 * | 8/2002 | Lohray et al. ............ 514/225.2 |

FOREIGN PATENT DOCUMENTS

| EP | 0 903 343 A1 | 3/1999 |
| WO | WO 96/04260 | 2/1996 |
| WO | WO 96/04261 | 2/1996 |
| WO | WO 97/25042 | 7/1997 |
| WO | WO 97/31907 | 9/1997 |
| WO | WO 99/08501 | 2/1999 |
| WO | WO 99/16758 | 4/1999 |
| WO | WO 99/19313 | 4/1999 |

OTHER PUBLICATIONS

Lohray et al., Chemical Abstracts, vol. 132:293769, 2000.*
Kirk-Othmer Encyclopedia of Chemical Technology Copyright © 2002 by John Wiley & Sons, Inc., pp. 95-147.*
Chemical & Engineering News, Feb. 24, 2003, pp. 32-35.*

* cited by examiner

*Primary Examiner*—Karl Puttlitz
(74) *Attorney, Agent, or Firm*—MacCord Mason PLLC

(57) ABSTRACT

The present invention relates to crystalline R-guanidines of (2S)-2-Ethoxy-3-{4-[2-(10H-phenoxazin-10-yl)ethoxy] phenyl}propanoate, its preparations and its use as therapeutic agents. More specifically the present invention relates to crystalline Arginine (2S)-2-Ethoxy-3-{4-[2-(10H-phenoxazin-10-yl)ethoxy]phenyl}propanoate, preferably (L)-Arginine (2S)-2-Ethoxy-3-{4-[2-(10H-phenoxazin-10-yl)ethoxy] phenyl}propanoate, its preparation and its use as therapeutic agent.

37 Claims, No Drawings

CRYSTALLINE R-GUANIDINES, ARGININE OR (L)-ARGININE (2S)-2-ETHOXY-3-{4-[2-(10H-PHENOXAZIN-10-YL) ETHOXY]PHENYL}PROPANOATE

CROSS REFERENCE TO RELATED APPLICATIONS

This application is a continuation of application Ser. No. 10/209,567 filed on Jul. 30, 2002, now abandoned and claims priority under 35 U.S.C. 119 of Danish application PA 1999 00536 filed on Apr. 20, 1999, of U.S. Provisional application 60/132,636 filed on May 5, 1999 and of PCT/IB99/00681 filed on Apr. 16, 1999, and the benefit of application Ser. No. 09/550,843 filed on Apr. 17, 2000 in the U.S. is claimed under 35 U.S.C. 120, the contents of which are fully incorporated herein by reference.

FIELD OF INVENTION

The present invention relates to crystalline R-guanidines of (2S)-2-Ethoxy-3-{4-[2-(10H-phenoxazin-10-yl)ethoxy]phenyl}propanoate, its preparations and its use as therapeutic agents. More specifically the present invention relates to crystalline Arginine (2S)-2-Ethoxy-3-{4-[2-(10H-phenoxazin-10-yl)ethoxy]phenyl}propanoate, preferably (L)-Arginine (2S)-2-Ethoxy-3-{4-[2-(10H-phenoxazin-10-yl)ethoxy]phenyl}propanoate, its preparation and its use as therapeutic agent.

BACKGROUND OF THE INVENTION

Coronary artery disease (CAD) is the major cause of death in type 2 diabetic and metabolic syndrome patients (i.e. patients that fall within the 'deadly quartet' category of impaired glucose tolerance, insulin resistance, hypertriglyceridaemia and/or obesity).

The hypolipidaemic fibrates and antidiabetic thiazolidinediones separately display moderately effective triglyceride-lowering activities although they are neither potent nor efficacious enough to be a single therapy of choice for the dyslipidaemia often observed in type 2 diabetic or metabolic syndrome patients. The thiazolidinediones also potently lower circulating glucose levels of type 2 diabetic animal models and humans. However, the fibrate class of compounds are without beneficial effects on glycaemia. Studies on the molecular actions of these compounds indicate that thiazolidinediones and fibrates exert their action by activating distinct transcription factors of the peroxisome proliferator activated receptor (PPAR) family, resulting in increased and decreased expression of specific enzymes and apolipoproteins respectively, both key-players in regulation of plasma triglyceride content. Fibrates, on the one hand, are PPARα activators, acting primarily in the liver. Thiazolidinediones, on the other hand, are high affinity ligands for PPARγ acting primarily on adipose tissue.

Adipose tissue plays a central role in lipid homeostasis and the maintenance of energy balance in vertebrates. Adipocytes store energy in the form of triglycerides during periods of nutritional affluence and release it in the form of free fatty acids at times of nutritional deprivation. The development of white adipose tissue is the result of a continuous differentiation process throughout life. Much evidence points to the central role of PPARγ activation in initiating and regulating this cell differentiation. Several highly specialised proteins are induced during adipocyte differentiation, most of them being involved in lipid storage and metabolism. The exact link from activation of PPARγ to changes in glucose metabolism, most notably a decrease in insulin resistance in muscle, has not yet been clarified. A possible link is via free fatty acids such that activation of PPARγ induces Lipoprotein Lipase (LPL), Fatty Acid Transport Protein (FATP) and Acyl-CoA Synthetase (ACS) in adipose tissue but not in muscle tissue. This, in turn, reduces the concentration of free fatty acids in plasma dramatically, and due to substrate competition at the cellular level, skeletal muscle and other tissues with high metabolic rates eventually switch from fatty acid oxidation to glucose oxidation with decreased insulin resistance as a consequence.

PPARα is involved in stimulating β-oxidation of fatty acids. In rodents, a PPARα-mediated change in the expression of genes involved in fatty acid metabolism lies at the basis of the phenomenon of peroxisome proliferation, a pleiotropic cellular response, mainly limited to liver and kidney and which can lead to hepatocarcinogenesis in rodents. The phenomenon of peroxisome proliferation is not seen in man. In addition to its role in peroxisome proliferation in rodents, PPARα is also involved in the control of HDL cholesterol levels in rodents and humans. This effect is, at least partially, based on a PPARα-mediated transcriptional regulation of the major HDL apolipoproteins, apo A-I and apo A-II. The hypotriglyceridemic action of fibrates and fatty acids also involves PPARα and can be summarised as follows: (I) an increased lipolysis and clearance of remnant particles, due to changes in lipoprotein lipase and apo C-III levels, (II) a stimulation of cellular fatty acid uptake and their subsequent conversion to acyl-CoA derivatives by the induction of fatty acid binding protein and acyl-CoA synthase, (III) an induction of fatty acid β-oxidation pathways, (IV) a reduction in fatty acid and triglyceride synthesis, and finally (V) a decrease in VLDL production. Hence, both enhanced catabolism of triglyceride-rich particles as well as reduced secretion of VLDL particles constitutes mechanisms that contribute to the hypolipidemic effect of fibrates.

A number of compounds have been reported to be useful in the treatment of hyperglycemia, hyperlipidemia and hypercholesterolemia (U.S. Pat. No. 5,306,726, PCT Publications nos. WO 91/19702, WO 95/03038, WO 96/04260, WO 94/13650, WO 94/01420, WO 97/36579, WO 97/25042, WO 95/17394, WO 99/08501, WO 99/19313 and WO 99/16758).

SUMMARY OF THE INVENTION

It seems more and more apparent that glucose lowering as a single approach does not over-come the macrovascular complications associated with type 2 diabetes and metabolic syndrome. Novel treatments of type 2 diabetes and metabolic syndrome must therefore aim at lowering both the overt hypertriglyceridaemia associated with these syndromes as well as alleviation of hyperglycaemia.

The clinical activity of fibrates and thiazolidinediones indicates that research for compounds displaying combined PPARα and PPARγ activation should lead to the discovery of efficacious glucose and triglyceride lowering drugs that have great potential in the treatment of type 2 diabetes and the metabolic syndrome (i.e. impaired glucose tolerance, insulin resistance, hypertriglyceridaemia and/or obesity).

Within one aspect, the present invention provides crystalline R-guanidines of (2S)-2-Ethoxy-3-{4-[2-(10H-phenoxazin-10-yl)ethoxy]phenyl}propanoate (pure or substantially pure), wherein R is defined as straight or branched alkyl, straight or branched alkenyl, or straight or branched alkynyl, each of which is optionally substituted with one or more halogen(s), —OH, —CF$_3$, —CN, C$_{1-4}$-alkoxy, C$_{1-4}$-alkylthio, —SCF$_3$, —OCF$_3$, —CONH$_2$, —CSNH$_2$, NH$_2$ or COOH.

In a preferred embodiment R is straight or branched alkyl optionally substituted with NH$_2$ and COOH.

In another preferred embodiment, R is straight or branched alkyl.

Within another aspect, the present invention provides crystalline Arginine (2S)-2-Ethoxy-3-{4-[2-(10H-phenoxazin-10-yl)ethoxy]phenyl}propanoate (pure or substantially pure).

Within another aspect, the present invention provides crystalline (L)-Arginine (2S)-2-Ethoxy-3-{4-[2-(10H-phenoxazin-10-yl)ethoxy]phenyl}propanoate (pure or substantially pure).

Within another aspect, the invention there is provided pharmaceutical compositions comprising crystalline R-guanidines of (2S)-2-Ethoxy-3-{4-[2-(10H-phenoxazin-10-yl)ethoxy]phenyl}propanoate optionally in combination with a pharmaceutically acceptable carrier or diluent.

Within another aspect of the invention there is provided pharmaceutical composition comprising crystalline Arginine (2S)-2-Ethoxy-3-{4-[2-(10H-phenoxazin-10-yl)ethoxy]phenyl}propanoate optionally in combination with a pharmaceutically acceptable carrier or diluent.

Within another aspect of the invention there is provided pharmaceutical composition comprising crystalline (L)-Arginine (2S)-2-Ethoxy-3-{4-[2-(10H-phenoxazin-10-yl)ethoxy]phenyl}propanoate optionally in combination with a pharmaceutically acceptable carrier or diluent.

Within another aspect of the invention there is provided a process for the preparation of crystalline R-guanidines of (2S)-2-Ethoxy-3-{4-[2-(10H-phenoxazin-10-yl)ethoxy]phenyl}propanoate which process comprises dissolving (2S)-2-Ethoxy-3-{4-[2-(10H-phenoxazin-10-yl)ethoxy]phenyl}propanoic acid in an appropriate organic solvent or a mixture of solvents and adding an R-guanidine in crystal form, as a suspension or dissolved in an appropiate solvent or a mixture of solvents and crystallizing the resulting salt from the solution.

Within another aspect of the invention there is provided a process for the preparation of crystalline Arginine (2S)-2-Ethoxy-3-{4-[2-(10H-phenoxazin-10-yl)ethoxy]phenyl}propanoate which process comprises dissolving (2S)-2-Ethoxy-3-{4-[2-(10H-phenoxazin-10-yl)ethoxy]phenyl}propanoic acid in an appropriate organic solvent or a mixture of solvents and adding Arginine in crystal form, as a suspension or dissolved in an appropiate solvent or a mixture of solvents and crystallizing the resulting salt from the solution.

Within another aspect of the invention there is provided a process for the preparation of crystal-line (L)-Arginine (2S)-2-Ethoxy-3-{4-[2-(10H-phenoxazin-10-yl)ethoxy]phenyl}propanoate which process comprises dissolving (2S)-2-Ethoxy-3-{4-[2-(10H-phenoxazin-10-yl)ethoxy]phenyl}propanoic acid in an appropriate organic solvent or a mixture of solvents and adding (L)-Arginine in crystal form, as a suspension or dissolved in an appropiate solvent or a mixture of solvents and crystallizing the resulting salt from the solution.

Within another aspect of the present invention there is provided a method of using the compounds according to the invention for the treatment and/or prevention of diabetes and/or obesity.

DETAILED DESCRIPTION OF THE INVENTION

Accordingly, the present invention relates to crystalline R-guanidines of (2S)-2-Ethoxy-3-{4-[2-(10H-phenoxazin-10-yl)ethoxy]phenyl}propanoate.

Further, the present invention relates to crystalline Arginine (2S)-2-Ethoxy-3-{4-[2-(10H-phenoxazin-10-yl)ethoxy]phenyl}propanoate.

Further, the present invention relates to crystalline (L)-Arginine (2S)-2-Ethoxy-3-{4-[2-(10H-phenoxazin-10-yl)ethoxy]phenyl}propanoate, hereinafter called compound I.

The present invention also relates to a process for the preparation of the above said novel compounds with advantageous physico-chemical characteristics compared to the free acid, and pharmaceutical compositions containing the compounds.

However, for commercial use it is important to have a physiologically acceptable salt with good stability, non-hygroscopicity, high melting point, high degree of crystallinity, good bioavailability, good handling properties and a reproducible crystalline form.

The free acid of this salt, (2S)-2-Ethoxy-3-{4-[2-(10H-phenoxazin-10-yl)ethoxy]phenyl}propanoic acid shows some pharmaceutically undesirable properties when looking for a suitable way of formulating the drug. It has a low melting point at around 88° C., undergoes a phase transformation at around 75° C. and is sparingly soluble in aqueous media. For the choice of a tablet formulation process it would be a big advantage to have a salt with a higher melting point and without phase transformation, that might be initiated by the tabletting process.

However, the (L)-Arginine salt was found to have advantageous physico-chemical characteristics that will significantly ease the formulation process. It has a high melting point at around 181° C., is highly stable, not hygroscopic even at relative humidities as high as 90 RH, shows a high degree of crystallinity, good bioavailability due to a significantly higher aqueous solubility, good handling properties, and appears in a reproducible crystalline form. Accordingly, the present invention provides compound I as a novel material, in particular in pharmaceutically acceptable form.

The present invention also provides a process for the preparation of crystalline R-guanidines of (2S)-2-Ethoxy-3-{4-[2-(10H-phenoxazin-10-yl)ethoxy]phenyl}propanoate which process comprises dissolving (2S)-2-Ethoxy-3-{4-[2-(10H-phenoxazin-10-yl)ethoxy]phenyl}propanoic acid in an appropriate organic solvent or a mixture of solvents and adding an R-guanidine in crystal form, as a suspension or dissolved in an appropiate solvent or a mixture of solvents and crystallizing the resulting salt from the solution.

The present invention also provides a process for the preparation of crystalline Arginine (2S)-2-Ethoxy-3-{4-[2-(10H-phenoxazin-10-yl)ethoxy]phenyl}propanoate which process comprises dissolving (2S)-2-Ethoxy-3-{4-[2-(10H-phenoxazin-10-yl)ethoxy]phenyl}propanoic acid in an appropriate organic solvent or a mixture of solvents and adding Arginine in crystal form, as a suspension or dissolved in an appropiate solvent or a mixture of solvents and crystallizing the resulting salt from the solution.

The present invention also provides a process for the preparation of compound I which process comprises dissolving (2S)-2-Ethoxy-3-{4-[2-(10H-phenoxazin-10-yl)ethoxy]phenyl}propanoic acid in an appropriate organic solvent or a mixture of solvents and adding (L)-Arginine in crystal form, as a suspension or dissolved in an appropriate solvent or mixture of solvents and crystallizing the resulting salt from the solution, or by other processes by which compound I can be prepared. Preferably (L)-Arginine is dissolved in water before added to (2S)-2-Ethoxy-3-{4-[2-(10H-phenoxazin-10-yl)ethoxy]phenyl}propanoic acid.

Examples of organic solvents include but are not limited to alcohol's as e.g. methanol, ethanol, 1-propanol, 2-propanol, butanol's or other organic solvents as e.g. acetonitrile, dioxane, tetrahydrofurane, ethers as e.g. t-butylmethylether, N,N-dimethylformamide, N-methyl-2-pyrrolidinone, sulfolane, dimethylsulfoxide, 1,3-dimethyl-3,4,5,6-tetrahydroxy-2(1H)-pyrimidinone.

Furthermore, the present compounds of formula I can be utilised in the treatment and/or prevention of conditions mediated by nuclear receptors, in particular the Peroxisome Proliferator-Activated Receptors (PPAR).

In a further aspect, the present invention relates to a method of treating and/or preventing Type I or Type II diabetes.

In a still further aspect, the present invention relates to the use of one or more compounds of the invention for the preparation of a medicament for the treatment and/or prevention of Type I or Type II diabetes.

In a still further aspect, the present compounds are useful for the treatment and/or prevention of IGT.

In a still further aspect, the present compounds are useful for the treatment and/or prevention of Type 2 diabetes.

In a still further aspect, the present compounds are useful for the delaying or prevention of the progression from IGT to Type 2 diabetes.

In a still further aspect, the present compounds are useful for the delaying or prevention of the progression from non-insulin requiring Type 2 diabetes to insulin requiring Type 2 diabetes.

In another aspect, the present compounds reduce blood glucose and triglyceride levels and are accordingly useful for the treatment and/or prevention of ailments and disorders such as diabetes and/or obesity.

In still another aspect, the present compounds are useful for the treatment and/or prophylaxis of insulin resistance (Type 2 diabetes), impaired glucose tolerance, dyslipidemia, disorders related to Syndrome X such as hypertension, obesity, insulin resistance, hyperglycaemia, atherosclerosis, hyperlipidemia, coronary artery disease, myocardial ischemia and other cardiovascular disorders.

In still another aspect, the present compounds are effective in decreasing apoptosis in mammalian cells such as beta cells of Islets of Langerhans.

In still another aspect, the present compounds are useful for the treatment of certain renal diseases including glomerulonephritis, glomerulosclerosis, nephrotic syndrome, hypertensive nephrosclerosis.

In still another aspect, the present compounds may also be useful for improving cognitive functions in dementia, treating diabetic complications, psoriasis, polycystic ovarian syndrome (PCOS) and prevention and treatment of bone loss, e.g. osteoporosis.

Furthermore, the invention relates to the use of the present compounds and pharmaceutically acceptable salts thereof for the preparation of a pharmaceutical composition for the treatment and/or prevention of conditions mediated by nuclear receptors, in particular the Peroxisome Proliferator-Activated Receptors (PPAR) such as the conditions mentioned above.

The present invention also provides pharmaceutical compositions comprising a crystalline compound of the present invention optionally in combination with a pharmaceutically acceptable carrier or diluent.

Pharmaceutical compositions containing a crystalline compound of the present invention and optionally other compounds as mentioned underneath may be prepared by conventional techniques, e.g. as described in Remington: The Science and Practise of Pharmacy, 19$^{th}$ Ed., 1995. The compositions may appear in conventional forms, for example capsules, tablets, aerosols, solutions, suspensions or topical applications.

The present compounds may also be administered in combination with one or more further pharmacologically active substances eg. selected from antiobesity agents, antidiabetics, antihypertensive agents, agents for the treatment and/or prevention of complications resulting from or associated with diabetes and agents for the treatment and/or prevention of complications and disorders resulting from or associated with obesity.

Thus, in a further aspect of the invention the present compounds may be administered in combination with one or more antiobesity agents or appetite regulating agents.

Such agents may be selected from the group consisting of CART (cocaine amphetamine regulated transcript) agonists, NPY (neuropeptide Y) antagonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 agonists, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, RXR (retinoid X receptor) modulators or TR β agonists.

In one embodiment of the invention the antiobesity agent is leptin.

In another embodiment the antiobesity agent is dexamphetamine or amphetamine.

In another embodiment the antiobesity agent is fenfluramine or dexfenfluramine.

In still another embodiment the antiobesity agent is sibutramine.

In a further embodiment the antiobesity agent is orlistat.

In another embodiment the antiobesity agent is mazindol or phentermine.

Suitable antidiabetics comprise insulin, GLP-1 (glucagon like peptide-1) derivatives such as those disclosed in WO 98/08871 to Novo Nordisk A/S, which is incorporated herein by reference as well as orally active hypoglycaemic agents.

The orally active hypoglycaemic agents preferably comprise sulphonylureas, biguanides, meglitinides, glucosidase inhibitors, glucagon antagonists such as those disclosed in WO 99/01423 to Novo Nordisk A/S and Agouron Pharmaceuticals, Inc., GLP-1 agonists, potassium channel openers such as those disclosed in WO 97/26265 and WO 99/03861 to Novo Nordisk A/S which are incorporated herein by reference, DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism such as antihyperlipidemic agents and antilipidemic agents as HMG CoA inhibitors (statins), compounds lowering food intake, RXR agonists and agents acting on the ATP-dependent potassium channel of the β-cells.

In one embodiment of the invention the present compounds are administered in combination with insulin.

In a further embodiment the present compounds are administered in combination with a sulphonylurea eg. tolbutamide, glibenclamide, glipizide or glicazide.

In another embodiment the present compounds are administered in combination with a biguanide eg. mefformin.

In yet another embodiment the present compounds are administered in combination with a meglitinide eg. repaglinide.

In a further embodiment the present compounds are administered in combination with an α-glucosidase inhibitor eg. miglitol or acarbose.

In another embodiment the present compounds are administered in combination with an agent acting on the ATP-dependent potassium channel of the β-cells eg. tolbutamide, glibenclamide, glipizide, glicazide or repaglinide.

Furthermore, the present compounds may be administered in combination with nateglinide.

In still another embodiment the present compounds are administered in combination with an antihyperlipidemic agent or antilipidemic agent eg. cholestyramine, colestipol, clofibrate, gemfibrozil, lovastatin, pravastatin, simvastatin, probucol or dextrothyroxine.

In a further embodiment the present compounds are administered in combination with more than one of the above-mentioned compounds eg. in combination with a sulphonylurea and mefformin, a sulphonylurea and acarbose, repaglinide and mefformin, insulin and a sulphonylurea, insulin and mefformin, insulin, insulin and lovastatin, etc.

Furthermore, the present compounds may be administered in combination with one or more antihypertensive agents. Examples of antihypertensive agents are β-blockers such as alprenolol, atenolol, timolol, pindolol, propranolol and metoprolol, ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin. Further reference can be made to Remington: The Science and Practice of Pharmacy, 19$^{th}$ Edition, Gennaro, Ed., Mack Publishing Co., Easton, Pa., 1995.

It should be understood that any suitable combination of the compounds according to the invention with one or more of the above-mentioned compounds and optionally one or more further pharmacologically active substances are considered to be within the scope of the present invention.

Typical compositions include a crystalline compound of the present invention associated with a pharmaceutically acceptable excipient which may be a carrier or a diluent or be diluted by a carrier, or enclosed within a carrier which can be in the form of a capsule, sachet, paper or other container. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohol's, polyethylene glycol's, polyhydroxyethoxylated castor oil, peanut oil, olive oil, gelatine, lactose, terra alba, sucrose, cyclodextrin, amylose, magnesium stearate, talc, gelatine, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent may include any sustained release material known in the art, such as glyceryl monostearate or glyceryl distearate, alone or mixed with a wax. The formulations may also include wetting agents, emulsifying and suspending agents, preserving agents, sweetening agents or flavouring agents. The formulations of the invention may be formulated so as to provide quick, sustained, or delayed release of the active ingredient after administration to the patient by employing procedures well known in the art.

The pharmaceutical compositions can be sterilized and mixed, if desired, with auxiliary agents, emulsifiers, salt for influencing osmotic pressure, buffers and/or colouring substances and the like, which do not deleteriously react with the active compound.

The route of administration may be any route, which effectively transports the active compound to the appropriate or desired site of action, such as oral, nasal, pulmonary, transdermal or parenteral e.g. rectal, depot, subcutaneous, intravenous, intraurethral, intramuscular, intranasal, ophthalmic solution or an ointment, the oral route being preferred.

If a solid carrier is used for oral administration, the preparation may be tabletted, placed in a hard gelatine capsule in powder or pellet form or it can be in the form of a troche or lozenge. If a liquid carrier is used, the preparation may be in the form of a syrup, emulsion, soft gelatine capsule or sterile injectable liquid such as an aqueous or non-aqueous liquid suspension or solution.

For nasal administration, the preparation may contain the compound of the present invention dissolved or suspended in a liquid carrier, in particular an aqueous carrier, for aerosol application. The carrier may contain additives such as solubilizing agents, e.g. propylene glycol, surfactants, absorption enhancers such as lecithin (phosphatidylcholine) or cyclodextrin, or preservatives such as parabenes.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet which may be prepared by conventional tabletting techniques may contain:

| Core: | |
|---|---|
| Active compound | 5 mg |
| Colloidal silicon dioxide (Aerosil) | 1.5 mg |
| Cellulose, microcryst. (Avicel) | 70 mg |
| Modified cellulose gum (Ac-Di-Sol) | 7.5 mg |
| Magnesium stearate | Ad. |
| Coating: | |
| HPMC approx. | 9 mg |
| *Mywacett 9-40 T approx. | 0.9 mg |

*Acylated monoglyceride used as plasticizer for film coating.

The compounds of the invention may be administered to a mammal, especially a human in need of such treatment, prevention, elimination, alleviation or amelioration of diseases related to the regulation of blood sugar.

Such mammals include also animals, both domestic animals, e.g. household pets, and nondomestic animals such as wildlife.

The compounds of the invention are effective over a wide dosage range. For example, in the treatment of adult humans, dosages from about 0.05 to about 100 mg, preferably from about 0.1 to about 100 mg, per day may be used. A most preferable dosage is about 0.1 mg to about 70 mg per day. In choosing a regimen for patients it may frequently be necessary to begin with a dosage of from about 2 to about 70 mg per day and when the condition is under control to reduce the dosage as low as from about 0.1 to about 10 mg per day. The exact dosage will depend upon the mode of administration, on the therapy desired, form in which administered, the subject to be treated and the body weight of the subject to be treated, and the preference and experience of the physician or veterinarian in charge.

Generally, the compounds of the present invention are dispensed in unit dosage form comprising from about 0.1 to about 100 mg of active ingredient together with a pharmaceutically acceptable carrier per unit dosage.

Usually, dosage forms suitable for oral, nasal, pulmonary or transdermal administration comprise from about 0.001 mg to about 100 mg, preferably from about 0.01 mg to about 50 mg of the compound of the invention admixed with a pharmaceutically acceptable carrier or diluent.

Pharmacological Methods

In vitro PPAR Alpha and PPAR Gamma Activation Activity.

Principle

The PPAR gene transcription activation assays were based on transient transfection into human HEK293 cells of two plasmids encoding a chimeric test protein and a reporter protein respectively. The chimeric test protein was a fusion of the DNA binding domain (DBD) from the yeast GAL4 transcription factor to the ligand binding domain (LBD) of the human PPAR proteins. The PPAR LBD harbored in addition to the ligand binding pocket also the native activation domain (activating function 2=AF2) allowing the fusion protein to function as a PPAR ligand dependent transcription factor. The GAL4 DBD will force the fusion protein to bind only to Gal4 enhancers (of which none existed in HEK293 cells). The reporter plasmid contained a Gal4 enhancer driving the expression of the firefly luciferase protein. After transfection, HEK293 cells expressed the GAL4-DBD-PPAR-LBD fusion protein. The fusion protein will in turn bind to the Gal4 enhancer controlling the luciferase expression, and do nothing the absence of ligand. Upon addition to the cells of a PPAR ligand, luciferase protein will be produced in amounts corresponding to the activation of the PPAR protein. The amount of luciferase protein is measured by light emission after addition of the appropriate substrate.

Methods

Cell culture and transfection: HEK293 cells were grown in DMEM+10% FCS, 1% PS. Cells were seeded in 96-well plates the day before transfection to give a confluency of 80% at transfection. 0.8 μg DNA per well was transfected using FuGene transfection reagent according to the manufacturers instructions (Boehringer-Mannheim). Cells were allowed to express protein for 48 h followed by addition of compound.

Plasmids: Human PPAR α and γ was obtained by PCR amplification using cDNA templates from liver, intestine and adipose tissue respectively. Amplified cDNAs were cloned into pCR2.1 and sequenced. The LBD from each isoform PPAR was generated by PCR (PPARα: aa 167-C-term; PPARγ: aa 165-C-term) and fused to GAL4-DBD by sub-cloning fragments in frame into the vector pM1 generating the plasmids pM1αLBD and pM1γLBD. Ensuing fusions were verified by sequencing. The reporter was constructed by inserting an oligonucleotide encoding five repeats of the Gal4 recognition sequence into the pGL2 vector (Promega).

Compounds: All compounds were dissolved in DMSO and diluted 1:1000 upon addition to the cells. Cells were treated with compound (1:1000 in 200 μl growth medium including delipidated serum) for 24 h followed by luciferase assay.

Luciferase assay: Medium including test compound was aspirated and 100 μl PBS incl. 1 mM Mg++ and Ca++ was added to each well. The luciferase assay was performed using the LucLite kit according to the manufacturers instructions (Packard Instruments). Light emission was quantified by counting SPC mode on a Packard Instruments top-counter.

The present invention is further illustrated by the following examples which, however, are not to be construed as limiting the scope of protection. The features disclosed in the foregoing description and in the following examples may, both separately and in any combination thereof, be material for realising the invention in diverse forms thereof.

Crystalline (L)-Arginine (2S)-2-Ethoxy-3-{4-[2-(10H-phenoxazin-10-yl)ethoxy]phenyl}propanoate was synthesized, purified and crystallized as described in the following example. Any novel feature or combination of features described herein is considered essential to this invention.

EXAMPLES

Synthesis of (2S)-2-Ethoxy-3-{4-[2-(10H-phenoxazin-10-yl)ethoxy]phenyl}propanoic acid Materials All solvents and reagents were purchased from Aldrich and Merck and used without further purification.

Ethyl-2-(10H-phenoxazin-10-yl)acetate

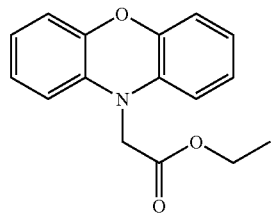

A solution of phenoxazine (10 g, 54.6 mmol) in dry dimethyl formamide (15 ml) was added slowly to a stirred ice cooled suspension of sodium hydride (60% dispersion in oil) (2.88 g, 60.1 mmol) in dimethyl formamide (10 ml), under an atmosphere of nitrogen. The mixture was stirred at 80° C. for 2 h and cooled to 0° C. and ethyl bromoacetate (12.78 g, 76.50 mmol) was added dropwise and stirring was continued for 12 h at 25° C. (TLC monitored). Water (50 ml) was added and the aqueous phase extracted with ethyl acetate (2×75 ml). The combined organic phases were washed with water (50 ml), brine (5 ml), dried (Na$_2$SO$_4$), filtered and the solvent was evaporated under reduced pressure. The residue was chromatographed over silica gel (100-200 mesh) using a mixture of benzene and petroleum ether (1:1) to afford the title compound (5.7 g, 39%) as a pale bluish green solid. mp: 96-97° C.

Note: DMF should be perfectly dry.

TLC Conditions:

TLC (visualised in UV and $I_2$) Eluent:Benzene:Petroleum ether (1:1), $R_f$=0.6.

2-(10H-Phenoxazin-10-yl)-1-ethanol

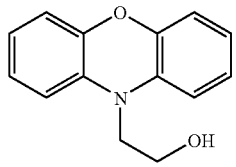

A solution of ethyl-2-(10H-phenoxazin-10-yl)acetate (5.5 g, 20.44 mmol) in dry tetrahydrofuran (20 ml) was added dropwise to a suspension of lithium aluminum hydride (1.16 g, 30.52 mmol) in dry tetrahydrofurane (20 ml) at 0° C. The reaction mixture was warmed to room temperature and stirred for additional 1 h. The excess lithium aluminum hydride was quenched with a solution of saturated sodium sulfate at 0° C. The reaction mixture was filtered and the residue was washed with hot ethyl acetate (2×75 ml). The combined organic layers were dried ($Na_2SO_4$), filtered and the solvent was evaporated under reduced pressure to afford the title compound (4.6 g, 99%) as a colourless solid. The compound is used in the next step without further purification. mp: 113-115° C.

TLC Conditions:

TLC (visualised in UV and $I_2$); Eluent, EtOAc:Petroleum ether (3:7), $R_f$=0.3.

2-(10H-Phenoxazin-10-yl)ethyl methanesulfonate

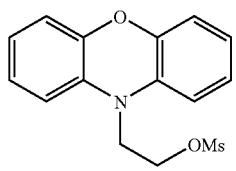

To a solution of 2-(10H-phenoxazin-10-yl)-1-ethanol (4.6 g, 20.28 mmol) in dichloromethane (20 ml) was added triethylamine (1.06 g, 10.56 mmol) under an atmosphere of nitrogen at 25° C. Methanesulfonyl chloride (0.90 g, 7.92 mmol) was added to the above reaction mixture at 0° C. and stirring was continued for further 3 h at 25° C. Water (50 ml) was added, and aqueous phase extracted with chloroform (2×25 ml). The combined organic phases were washed with water (25 ml), dried ($Na_2SO_4$), filtered and the solvent was evaporated under reduced pressure. The residue was triturated with petroleum ether to afford the title compound (5.7 g, 92%) as a solid. mp: 81-83° C.

TLC Conditions:

TLC (visualised in UV and $I_2$); Eluent:MEOH:$CHCl_3$ (1:99), $R_f$=0.6.

Ethyl-(E/Z)-3-[4-(benzyloxy)phenyl]-2-ethoxy-propenoate

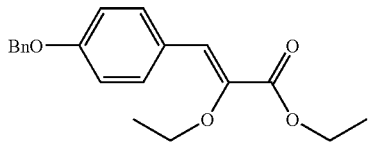

A solution of triethyl-2-ethoxyphosphonoacetate (9) prepared by the method of Grell and Machleidt, *Annalen. Chemie*, 1996, 699, 53 (3.53 g, 13.2 mmol) in dry tetrahydrofurane (10 ml) was added slowly to a stirred ice cooled suspension of sodium hydride (60% dispersion of oil) (0.62 g, 12.97 mmol) in dry tetrahydrofuran (5 ml), under an atmosphere of nitrogen. The mixture was stirred at 0° C. for 30 min followed by the addition of 4-benzyloxybenzaldehyde (2.5 g, 11.79 mmol) dissolved in dry tetrahydrofurane (20 ml). The mixture was allowed to warm to room temperature and stirred for additional 20 h. The excess sodium hydride was quenched with a few drops of cold water. The solvent was evaporated, water (100 ml) was added and the aqueous phase extracted with ethyl acetate (2×75 ml). The combined organic extracts were washed with water (50 ml), brine (50 ml), dried ($Na_2SO_4$), filtered and the solvent was evaporated under reduced pressure. The residue was chromatographed over silica gel using a mixture of ethyl acetate and petroleum ether (2:8) as the eluent to afford the title compound (3.84 g, quantitative) as an oil. $^1H$ NMR of the product suggests a (76: 24=Z:E) mixture of geometric isomers (R. A. Aitken and G. L. Thom, *Synthesis*, 1989, 958).

TLC Conditions:

TLC (visualised in UV and $I_2$); Eluent, EtOAc:petroleum ether (1:9), 2 spots (E/Z isomers), $R_f$=0.48 and 0.46.

Note: This compound can be obtained as a pale yellow solid, mp: 50-52° C.

Ethyl-(2R/2S)-2-ethoxy-3-(4-hydroxyphenyl)propanoate

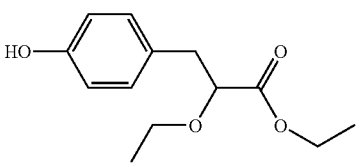

A suspension of ethyl Ethyl-(E/Z)-3-[4-(benzyloxy)phenyl]-2-ethoxy-propenoate (3.85 g, 11.80 mmol) and 10% Pd—C (0.30 g) in ethyl acetate (50 ml) was stirred at 25° C. under 60 psi of hydrogen pressure for 24 h. The catalyst was filtered off and the solvent was evaporated under reduced pressure. The residue was chromatographed over silica gel using a mixture of ethyl acetate and petroleum ether (2:8) to afford the title compound (1.73 g, 61%) as an oil.

TLC Conditions:

TLC (visualised in UV and $I_2$) Eluent, EtOAc:petroleum ether (1:5), $R_f$=0.35.

Ethyl-(2R/2S)-2-ethoxy 3-{4-[2-(10H-phenoxazin-10-yl)ethoxy]phenyl}propanoate

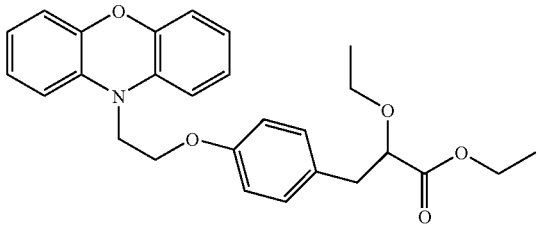

A mixture of 2-(10H-Phenoxazin-10-yl)ethyl methanesulfonate (0.5 g, 1.63 mmol), Ethyl-(2R/2S)-2-ethoxy-3-(4-hydroxyphenyl)propanoate (0.46 g, 1.9 mmol) and potassium carbonate (0.45 g, 3.2 mmol) in dry dimethyl formamide (20 ml) was stirred for 12 h at 80° C. The reaction mixture was cooled to room temperature. Water (40 ml) was added and the aqueous phase was extracted with ethyl acetate (2×50 ml). The combined organic phases were washed with water (50 ml), dried ($Na_2SO_4$) filtered and the solvent was evaporated under reduced pressure. The residue was chromatographed over silica gel (100-200 mesh) using a mixture of ethyl acetate and petroleum ether (1:9) to afford the title compound (0.55 g. 75%) as a white solid. mp: 51-53° C.

TLC (visualised in $I_2$); Eluent, EtOAc:petroleum ether (1:9), $R_f$=0.7.

(2R/2S)-2-Ethoxy-3-{4-[2-(10H-phenoxazin-10-yl)ethoxy]phenyl}propanoic acid

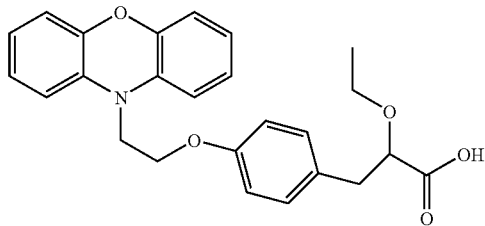

To a solution of Ethyl-(2R/2S)-2-ethoxy 3-{4-[2-(10H-phenoxazin-10-yl)ethoxy]phenyl}-propanoate (62 g, 138.7 mmol) in methanol (1000 ml) was added 10% aqueous sodium hydroxide solution (300 ml). The mixture was stirred at 25° C. for 6 h. Methanol was evaporated under reduced pressure, water (200 ml) was added and acidified with 2N hydrochloric acid. The mixture was extracted with ethyl acetate (3×500 ml). The combined organic phases were washed with water (2×500 ml), brine (500 ml), dried ($Na_2SO_4$), filtered and the solvent evaporated under reduced pressure. The residue was triturated with petroleum ether to afford the title compound (56 g, 96%) as a white solid. mp: 89-91° C.

TLC Conditions:
TLC (visualised in $I_2$); Eluent. EtOAc:petroleum ether (3:1)e, $R_f$=0.4.

HPLC Conditions:
Lichrosphere RP $C^{18}$-0.01 m $KH_2PO_4$:Acetonitrile, 25:75, (pH=3.0). Flow: 1 ml/min.
λmax: 245 nm.

Resolution of the (R/S) (+/−) form on chiral column.
Chiralcel—OJ, Hexane:EtOH:AcOH (90:10:0.3). Flow: 1.2 ml/min.
λmax=245 nm.
(+) form: $R_t$: 42. 40 min. (−) form: $R_t$=36.10 min.

(2S)-2-ethoxy-N-[(1S)-2-hydroxy-1-phenylethyl]-3-{4-[2-(10H-phenoxazin-10-yl)ethoxy]phenyl}propanamide

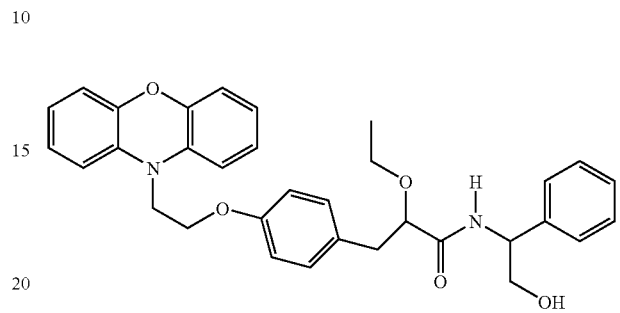

To an ice cooled solution (2R/2S)-2-Ethoxy-3-{4-[2-(10H-phenoxazin-10-yl]ethoxy]phenyl}propanoic acid (1.2 g, 2.9 mmol) and triethylamine (0.58 g. 5.8 mmol) in dry dichloromethane (25 ml) was added pivaloyl chloride (0.38 g, 3.19 mmol) and stirring was continued for 30 min at 0° C. A mixture of (S)-2-phenylglycinol (0.39 g, 2.9 mmol) and triethylamine (0.58 g, 5.8 mmol) in dichloromethane (20 ml) was added to the above reaction mixture at 0° C. and stirring was continued for 2 h at 25° C. Water (50 ml) was added and the aqueous phase extracted with dichloromethane (2×50 ml). The combined organic phases were washed with water (2×25 ml), brine (25 ml), dried ($Na_2SO_4$) and evaporated. The residue was chromatographed over silica gel using a gradient of 40-60% ethyl acetate in petroleum ether as an eluent to afford the two diastereomers: (2S)-2-ethoxy-N-[(1S)-2-hydroxy-1-phenylethyl]-3-{4-[2-(10H-phenoxazin-10-yl)ethoxy]phenyl}propanamide (0.55 g, 35%) and (2S)-2-ethoxy-N-[(1R)-2-hydroxy-1-phenylethyl]-3-{4-[2-(10H-phenoxazin-10-yl)ethoxy]phenyl}propanamide (0.5 g, 32%).

(2S)-2-Ethoxy-3-{4-[2-(10H-phenoxazin-10-yl)ethoxy]phenyl}propanoic acid

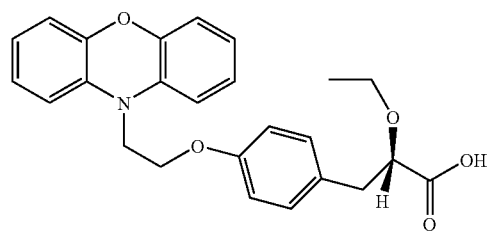

(2S)-2-Ethoxy-N-[(1S)-2-hydroxy-1-phenylethyl]-3-{4-[2-(10H-phenoxazin-10-yl)ethoxy]phenyl}propanamide (0.45 g, 0.84 mmol) was dissolved in a mixture of 1M sulphuric acid (17 ml) and dioxane/water (1:1.39 ml) and heated to 90° C. for 88 h. The pH of the mixture was adjusted to 3 by addition of an aqueous sodium hydrogen carbonate solution. The mixture was extracted with ethyl acetate (2×25 ml) and the organic phase was washed with water (50 ml), brine (25 ml), dried ($Na_2SO_4$) and evaporated. The residue was chromatographed over silica gel using a gradient of 50-75% ethyl acetate in petroleum ether to afford the title compound (0.19 g, 54%) as a white solid. mp: 89-90° C.

Syntheses of (L)-Arginine (2S)-2-Ethoxy-3-{4-[2-(10H-phenoxazin-10-yl)ethoxy]phenyl}-propanoate

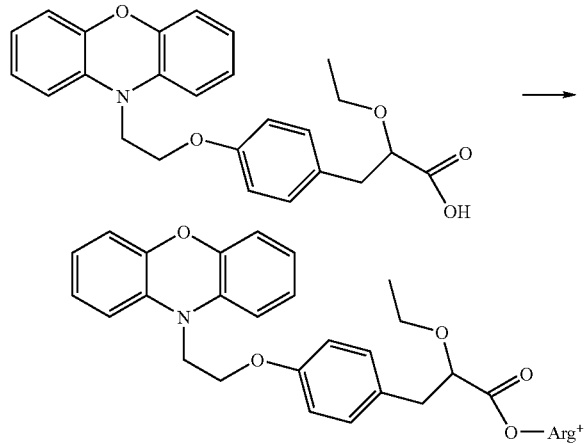

(2S)-2-Ethoxy-3-{4-[2-(10H-phenoxazin-10-yl)ethoxy]phenyl}propanoic acid (104.3 g; 249 mmol) was dissolved in ethanol (2.0 l), filtered (filter-paper) and transferred to a 4 l reactor. The used glass equipment was washed with ethanol (0.6 l) to get a quantitative transfer of the compound.

(L)-Arginine (43.38 g; 249 mmol) was dissolved in water (150 ml) at 50-60° C. and added to the solution of (2S)-2-ethoxy-3-{4-[2-(10H-phenoxazin-10-yl)ethoxy]phenyl}propanoic acid heated to 75-80° C. (The solution was homogeneous after the addition).

The mixture was cooled slowly to room temperature over night to get a precipitation (seeding can be an advantage in some cases). The following day the suspension was cooled to 0-5° C. and filtered. The product was washed with ethanol (100 ml×2) and dried in vacuum until no further weight loss could be detected. The process yielded 135 g; 91% of the title product.

Syntheses of (L)-Arginine (2S)-2-Ethoxy-3-{4-[2-(10H-phenoxazin-10-yl)ethoxy]phenyl}-propanoate (2S)-2-Ethoxy-3-{4-[2-(10H-phenoxazin-10-yl)ethoxy]phenyl}propanoic acid (300 mg; 0.72 mmol) was dissolved in isopropanol (3 ml), filtered and transferred to a flask.

(L)-Arginine (124.6 mg, 0.72 mmol) was dissolved in water (½ ml) at 50-60° C. and added to the solution of (2S)-2-Ethoxy-3-{4-[2-(10H-phenoxazin-10-yl)ethoxy]phenyl}propanoic acid, heated to reflux.

The mixture was kept for 10 days at 40° C., cooled to room temperature and filtered. The product was dried in vacuum. The process yielded 300 mg of the title product, M.p. 181° C.

Analytical data for (L)-Arginine (2S)-2-Ethoxy-3-{4-[2-(10H-phenoxazin-10-yl)ethoxy]phenyl}propanoate The crystals were characterised by the following methods: $^1$H-NMR spectra and elemental analysis.

$^1$H-NMR of Compound I used solvent: mixture of [$^2$H$_6$]DMSO (δ=2.49) and D$_2$O (δ=3.5)

| $^1$H | Chemical Shift δ (ppm) | Integral | Coupling Pattern | Coupling Constants $^nJ_{HH}$ (Hz) |
|---|---|---|---|---|
| H1, H2, H3, H4, H5, H6, H7, H8 | 6.6-6.9 | 8H | m | ND (=not determined) |
| H9, H9' | 4.15 | 2H | t | $^3J_{HH} = 6$ |
| H10, H10' | 3.97 | 2H | t | $^3J_{HH} = 6$ |
| H11, H14 | 6.77 | 2H | A-part of AB-pattern | $^3J_{HH} = 8$ |
| H12, H13 | 7.10 | 2H | B-part of AB-pattern | $^3J_{HH} = 8$ |
| H14 | 2.82 | 1H | dd | $^2J_{HH} = 14, ^3J_{HH} = 4$ |
| H14' | 2.63 | 1H | dd | $^2J_{HH} = 14, ^3J_{HH} = 9$ |
| H15 | 3.58 | 1H | dd | $^3J_{HH} = 4, ^3J_{HH} = 9$ |
| H16 | 3.52 | 1H | dq | $^2J_{HH} = 9.5, ^3J_{HH} = 7$ |
| H16' | 3.13 | 1H | dq | $^2J_{HH} = 9.5, ^3J_{HH} = 7$ |
| H17 | 0.97 | 3H | t | $^3J_{HH} = 7$ |
| H18 | 3.23 | 1H | t | $^3J_{HH} = 5$ |
| H19 | 1.65 | 1H | m | ND |
| H19' | 1.75 | 1H | m | ND |
| H20 | 1.57 | 2H | m | ND |
| H21 | 3.05 | 1H | m | ND |

Elemental Analysis

The elemental composition of compound I was determined as follows: Calculated composition data: C, 62.68%, H: 6.65%; N, 11.70% Found: C: 62.72%, H: 6.62%; N: 11.80%.

The invention claimed is:

1. A crystalline form of arginine (2S)-2-ethoxy-3-{4-[2-(10H-phenoxazin-10-yl)ethoxy]phenyl}-propanoate.

2. A crystalline form of (L)-arginine (2S)-2-ethoxy-3-{4-[2-(10H-phenoxazin-10-yl)ethoxy]phenyl}-propanoate, wherein the crystalline form has at least 1 proton (1H) NMR spectra selected from the group consisting of 6.6-6.9 (m, 8H), 4.15 (t, 2H, J=6), 7.10 (2H, J=8), 2.82 (dd, 1H, J=14, J=4), 2.63 (dd, 1H, J=14, J=9), 3.58 (dd, 1H, J=14, J=9), 3.52 (dq, 1H, J=9.5, J=7), 3.13 (dq, 1H, J=9.5, J=7), 0.97 (t, 3H, J=7), 3.23 (t, 1H, J=5), 1.65 (m, 1H), 1.75 (m, 1H), 1.57 (m, 2H), and 3.05 (m, 1H).

3. The crystalline compound of claim 2 wherein the proton (1H) NMR spectra is 6.6-6.9 (m, 8H), 4.15 (t, 2H, J=6), 3.97 (t, 2H, J=6), 6.77 (2H, J=8), 7.10 (2H, J=8), 2.82 (dd, 1H, J=14, J=4), 2.63 (dd, 1H, J=14, J=9), 3.58 (dd, 1H, J=14, J=9), 3.52 (dq, 1H, J=9.5, J=7), 3.13 (dq, 1H, J=9.5, J=7), 0.97 (t, 3H, J=7), 3.23 (t, 1H, J=5), 1.65 (m, 1H), 1.75 (m, 1H), 1.57 (m, 2H), 3.05 (m, 1H).

4. A process for the preparation of (L)-arginine (2S)-2-ethoxy-3-{4-[2-(10H-phenoxazin-10-yl)ethoxy]phenyl}-propanoate, which process comprises dissolving (2S)-2-ethoxy-3{4{2(10H-phenoxazin-10-yl)ethoxy]phenyl}propanoic acid in a solvent, adding (L)-arginine and crystallizing the resulting salt from the solution, wherein the crystalline form has at least 1 proton (1H) NMR spectra selected from the group consisting of 6.6-6.9 (m, 8H), 4.15 (t, 2H, J=6), 7.10 (2H, J=8), 2.82 (dd, 1H, J=14, J=4), 2.63 (dd, 1H, J=14, J=9), 3.58 (dd, 1H, J=14, J=9), 3.52 (dq, 1H, J=9.5, J=7), 3.13 (dq, 1H, J=9.5, J=7), 0.97 (t, 3H, J=7), 3.23 (t, 1H, J=5), 1.65 (m, 1H), 1.75 (m, 1H), 1.57 (m, 2H), and 3.05 (m, 1H).

5. The process according to claim 4 wherein said (L)-arginine is in a crystalline form.

6. The process according to claim 4 wherein said (L)-arginine is added as a suspension.

7. The process according to claim 4 wherein said (L)-arginine is dissolved in an appropriate solvent.

8. The process according to claim 7 wherein said solvent is water.

9. The process according to claim 4 wherein said (L)-arginine is dissolved in a mixture of solvents.

10. The process according to claim 4 wherein said (2S)-2-ethoxy-3{4{2(10H-phenoxazin-10-yl)ethoxy]phenyl}propanoic is dissolved in an organic solvent.

11. The process according to claim 4 wherein said (2S)-2-ethoxy-3{4{2-(10H-phenoxazin-10-yl)ethoxy]phenyl}propanoic is dissolved in a mixture of solvents.

12. A pharmaceutical composition comprising crystalline (L)-arginine (2S)-2-ethoxy-3-{4-[2-(10H-phenoxazin-10-yl)ethoxy]phenyl}propanoate together with a pharmaceutically acceptable carrier or diluent, wherein the crystalline form has at least 1 proton (1H) NMR spectra selected from the group consisting of 6.6-6.9 (m, 8H), 4.15 (t, 2H, J=6), 7.10 (2H, J=8), 2.82 (dd, 1H, J=14, J=4), 2.63 (dd, 1H, J=14, J=9), 3.58 (dd, 1H, J=14, J=9), 3.52 (dq, 1H, J=9.5, J=7), 3.13 (dq, 1H, J=9.5, J=7), 0.97 (t, 3H, J=7), 3.23 (t, 1H, J=5), 1.65 (m, 1H), 1.75 (m, 1H), 1.57 (m, 2H), and 3.05 (m, 1H).

13. A pharmaceutical composition according to claim 12 comprising from 0.001 to about 100 mg of crystalline (L)-Arginine (2S)-2-Ethoxy-3-{4-[2-(10H -phenoxazin-10yl)ethoxy]phenyl}propanoate.

14. A pharmaceutical composition according to claim 12, comprising from about 0.05 to about 100 mg of crystalline (L)-Arginine (2S)-2-Ethoxy-3-{4-[2-(10H-phenoxazin-10yl)ethoxy]phenyl}propanoate.

15. The pharmaceutical composition according to claim 12, comprising from about 0.1 to about 50 mg of crystalline (L)-Arginine (2S)-2-Ethoxy-3-{4-[2-(10H-phenoxazin-10yl)ethoxy]phenyl}propanoate.

16. The pharmaceutical composition according to claim 12 which is useful in the treatment and/or prevention of conditions mediated by nuclear receptors.

17. The pharmaceutical composition according to claim 15 wherein said nuclear receptor is peroxisome proliferators-activated receptor (PPAR).

18. The pharmaceutical composition according to claim 12 which is useful in the treatment of conditions associated with high blood glucose and high levels of triglyceride.

19. The pharmaceutical composition according to claim 18 wherein the condition is diabetes.

20. The pharmaceutical composition according to claim 18 wherein the condition is obesity.

21. The pharmaceutical composition according to claim 12 which is in the form of a tablet, capsule, powder, syrup, solution or suspension.

22. The pharmaceutical composition according to claim 12, wherein said composition is administered by a parenteral, oral, transdermal, pulmonary, or nasal route.

23. A method for the treatment of conditions associated with high blood glucose and/or triglyceride, which method comprises administering to a subject in need thereof an effective amount of crystalline (L)-Arginine (2S)-2-Ethoxy-3-{4-[2-(10H-phenoxazin-10-yl)ethoxy]phenyl}propanoate, wherein the crystalline form has at least 1 proton (1H) NMR spectra selected from the group consisting of 6.6-6.9 (m, 8H), 4.15 (t, 2H, J=6), 7.10 (2H, J=8), 2.82 (dd, 1H, J=14, J=4), 2.63 (dd, 1H, J=14, J=9), 3.58 (dd, 1H, J=14, J=9), 3.52 (dq, 1H, J=9.5, J=7), 3.13 (dq, 1H, J=9.5, J=7), 0.97 (t, 3H, J=7), 3.23 (t, 1H, J=5), 1.65 (m, 1H), 1.75 (m, 1H), 1.57 (m, 2H), and 3.05 (m, 1H).

24. The method of claim 23, wherein said condition is diabetes.

25. The method according to claim 23, wherein said condition is obesity.

26. The method according to claim 23 wherein said effective amount is in the range of from about 0.001 to about 100 mg per day.

27. The method according to claim 23 wherein said effective amount is in the range of from about 0.05 to about 100 mg per day.

28. The method according to claim 23 wherein the effective amount is in the range of from about 0.1 to about 50 mg per day.

29. The method according to claim 23, wherein said subject is a mammal.

30. The method according to claim 29, wherein said mammal is human.

31. A method for the treatment of conditions associated with high blood glucose and/or triglyceride, which method comprises administering to a subject in need thereof an effective amount of crystalline (L)-Arginine (2S)-2-Ethoxy-3-{4-[2-(10H-phenoxazin-10-yl)ethoxy]phenyl}propanoate in combination with one or more pharmacologically active substance, wherein the crystalline form has at least 1 proton (1H) NMR spectra selected from the group consisting of 6.6-6.9 (m, 8H), 4.15 (t, 2H, J=6), 7.10 (2H, J=8), 2.82 (dd, 1H, J=14, J=4), 2.63 (dd, 1H, J=14, J=9), 3.58 (dd, 1H, J=14, J=9), 3.52 (dq, 1H, J=9.5, J=7), 3.13 (dq, 1H, J=9.5, J=7), 0.97 (t, 3H, J=7), 3.23 (t, 1H, J=5), 1.65 (m, 1H), 1.75 (m, 1H), 1.57 (m, 2H), and 3.05 (m, 1H).

32. The method according to claim 31, wherein said active substance is an antiobesity agent.

33. The method according to claim 31, wherein said active substance is an appetite regulating agent.

34. The method according to claim 31, wherein said active substance is an antidiabetic agent.

35. The method according to claim 31, wherein said active substance is an antihypertensive agent.

36. A method for reducing blood glucose and/or triglyceride levels comprising administering to a subject in need thereof an inhibitory amount of crystalline (L)-Arginine (2S)-2-Ethoxy-3-{4-[2-(10H-phenoxazin-10-yl)ethoxy]phenyl}propanoate, wherein the crystalline form has at least 1 proton (1H) NMR spectra selected from the group consisting of 6.6-6.9 (m, 8H), 4.15 (t, 2H, J=6), 7.10 (2H, J=8), 2.82 (dd, 1H, J=14, J=4), 2.63 (dd, 1H, J=14, J=9), 3.58 (dd, 1H, J=14, J=9), 3.52 (dq, 1H, J=9.5, J=7), 3.13 (dq, 1H, J=9.5, J=7), 0.97 (t, 3H, J=7), 3.23 (t, 1H, J=5), 1.65 (m, 1H), 1.75 (m, 1H), 1.57 (m, 2H), and 3.05 (m, 1H).

37. A method for inhibiting a Peroxisome Proliferator-Activated Receptors (PPAR) in a cell comprising administering to said cell an inhibitory amount of crystalline (L)-Arginine (2S)-2-Ethoxy-3-{4-[2-(10H-phenoxazin-10-yl)ethoxy]phenyl}propanoate, wherein the crystalline form has at least 1 proton (1H) NMR spectra selected from the group consisting of 6.6-6.9 (m, 8H), 4.15 (t, 2H, J=6), 7.10 (2H, J=8), 2.82 (dd, 1H, J=14, J=4), 2.63 (dd, 1H, J=14, J=9), 3.58 (dd, 1H, J=14, J=9), 3.52 (dq, 1H, J=9.5, J=7), 3.13 (dq, 1H, J=9.5, J=7), 0.97 (t, 3H, J=7), 3.23 (t, 1H, J=5), 1.65 (m, 1H), 1.75 (m, 1H), 1.57 (m, 2H), and 3.05 (m, 1H).

* * * * *